United States Patent [19]

Schrader

[11] Patent Number: 4,714,345

[45] Date of Patent: Dec. 22, 1987

[54] SAMPLE ARRANGEMENT FOR SPECTROMETRY, METHOD FOR THE MEASUREMENT OF LUMINESCENCE AND SCATTERING AND APPLICATION OF THE SAMPLE ARRANGEMENT

[76] Inventor: Bernhard Schrader, Soniusweg 20, 4300 Essen, Fed. Rep. of Germany, 15

[21] Appl. No.: 749,882

[22] Filed: Jun. 27, 1985

[30] Foreign Application Priority Data

Jun. 29, 1984 [DE] Fed. Rep. of Germany ....... 3424108

[51] Int. Cl.$^4$ ..................... G01N 21/03; G01N 21/05; G01N 21/65
[52] U.S. Cl. ..................................... 356/246; 356/301
[58] Field of Search ................. 356/246, 301

[56] References Cited

U.S. PATENT DOCUMENTS

| | | | |
|---|---|---|---|
| 3,436,159 | 4/1969 | Harrick et al. | 356/256 |
| 3,486,829 | 12/1969 | Wilks, Jr. | 356/246 |
| 3,556,659 | 1/1971 | Hawes | 356/301 |
| 3,610,757 | 10/1971 | Valkenburg et al. | 356/246 X |
| 3,972,627 | 8/1976 | Rabl et al. | 356/246 |
| 4,088,407 | 5/1978 | Schoeffel et al. | 356/246 X |
| 4,090,789 | 5/1978 | Macemon et al. | 356/318 |
| 4,348,107 | 9/1982 | Leif | 356/246 X |
| 4,422,761 | 12/1983 | Frommer | 356/246 |

OTHER PUBLICATIONS

Jenkins & White "Fundamentals of Optics" McGraw-Hill Book Co. Inc., 1957, pp. 268-270.

Primary Examiner—Vincent P. McGraw

[57] ABSTRACT

The invention relates to a sample arrangement for spectrometry, especially Raman spectrometry, with an essentially spherical sample container of transparent material, in the center of which the sample is arranged, and a procedure for the measurement of luminescence and scattering, e.g. chemiluminescence, fluorescence, phosphorescence and Raman scattering as well as absorption wherein the sample arrangement is placed in the optical paths of an in principle known spectrometer.

8 Claims, 14 Drawing Figures

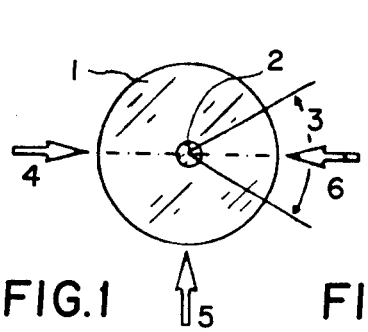
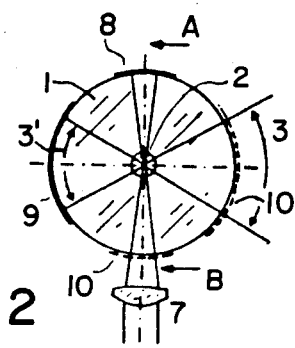
FIG.1   FIG.2
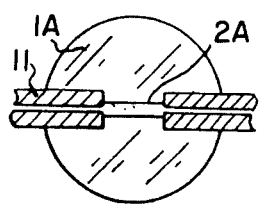
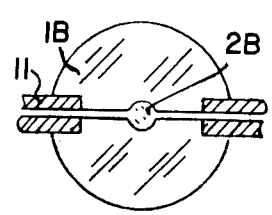
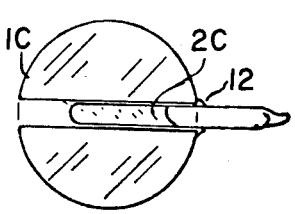
FIG.3   FIG.4   FIG.5
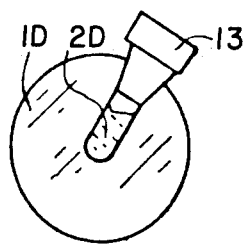
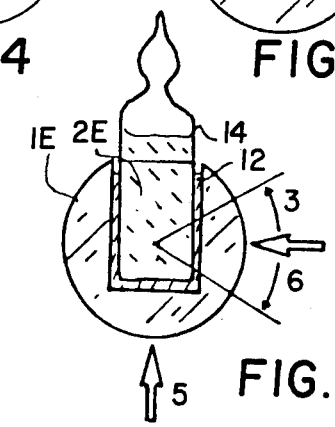
FIG.6   FIG.7
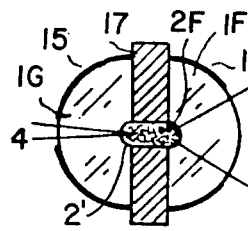
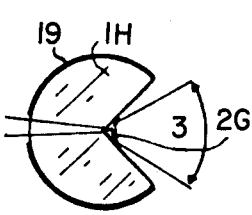
FIG.8   FIG.9   FIG.10
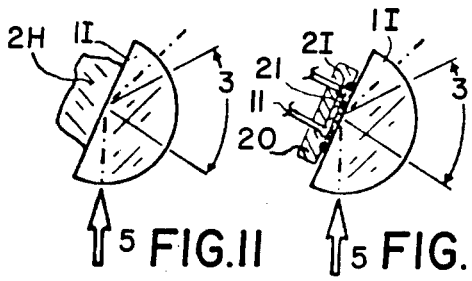
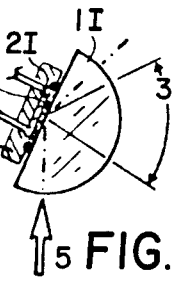
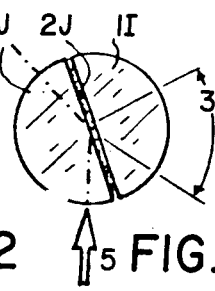
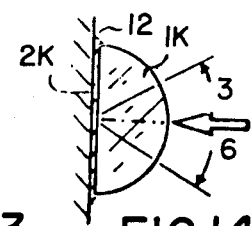
FIG.11   FIG.12   FIG.13   FIG.14

SAMPLE ARRANGEMENT FOR SPECTROMETRY, METHOD FOR THE MEASUREMENT OF LUMINESCENCE AND SCATTERING AND APPLICATION OF THE SAMPLE ARRANGEMENT

The invention is concerned with a sample arrangement for spectrometry, especially Raman spectrometry, with a method for the measurement of luminescence and scattering, for example chemiluminescence, fluorescence, phosphorescence and Raman scattering as well as absorption and the application of the sample arrangement; it is especially useful for the routine investigation of the spectra of solid, liquid and gaseous samples.

Raman scattering is extremely weak. In order to record LASER-excited Raman spectra of delicate samples with a diode-array spectrometer one has to use sample arrangements of high optical conductance. Theoretical discussions show (Ullmanns Encyklopaedie der technischen Chemie, 4. edition 1980, p. 303, Verlag Chemie, Weinheim) that the LASER radiation has to be focused and the sample has to be arranged at the focus. According to eq. 53 and 56 in the cited article the light flux from the sample through the spectrometer to the detector is inversely proportional to the diameter of the LASER beam at the focus, and proportional to the power of the LASER as well as to the solid angle of the Raman radiation of the sample 'seen' by the spectrometer. This means, that most intensive spectra are given from extremely small samples (dimensions of about several micrometers) when they are imaged into the entrance slit of a powerful spectrometer with a lens of extremely large aperture, provided that it is matched to the optical conductance of the spectrometer.

In conventional Raman spectrometers the samples are contained in rectangular or, more seldom, cylindrical cells (brochures of Spex Industries, Metuchen, N.J. (USA); Instruments S.A. Paris (France); Jenaoptic, Jena (GDR); Applied Photophysics, London (Great Britian); Jeol (Japan), as well as the cited article in Ullmans Encyclopaedia). These sample arrangements are not well suited for the illumination of extremely powerful spectrometers.

Due to the refraction at the window of the cell only a fraction of the light from the sample is imaged into the spectrometer. Further, also due to the refraction, the focus of the rays at the rim of the aperture cone is shifted with respect to the focus of the central rays. Therefore, a small sample in such a cell cannot be imaged properly into a powerful spectrometer. Further, also the focus of the LASER beam is blurred due to the refraction at the window of the sample cell. Finally it is extremely difficult to adjust the lase beam with respect to the beam of the observation optimally. Furthermore the adjustment parameters are altered, when the refractive index of the sample changes. Routine investigations are therefore difficult to be carried out. Commercial sample arrangements for micro samples use conventional microscope objective lenses. Since their optical conductance is already smaller than that of conventional spectrometers, they are not useful for the investigation of micro samples with extremely powerful spectrometers.

Analogous arguments are true for other spectrometric methods: The conventional rectangular or cylindrical cells are not well suited for the investigation of micro samples with powerful spectrometers.

The problem to be solved by the invention is to develop a sample arrangement for spectrometry, especially Raman spectrometry, which transfers a maximal flux of the radiation to be investigated from samples in any state of the matter into a spectrometer.

The invention describes a sample arrangement, which is characterized by an essentially spherical sample container of transparent material, in the center of which the sample is arranged. The invention relates essentially to a measuring procedure which is characterized by the application of the sample arrangement for luminescence, fluorescence, phosphorescence, Raman-, as well as absorption and scattering spectroscopy. Optimal matching of the micro sample to an extremely powerful spectrometer is achieved by an essentially spherical sample container of transparent material, in the center of which the sample is arranged, by imaging of the center of the sphere by an extremely powerful lens into the spectrometer, by focusing of the illuminating beam into the center of the sphere, with a reduction of the reflection on the surface for the illuminating and observed light and with reflecting layers on other parts of the surface of the sphere. Such 'aplanatic' sample arrangement guarantees that the focus of the illuminating and the observation optics is the same for beams with large or small angles with respect to the optical axis. Further advantages are:

1. The mirrors on the surface of the sphere reflect all exciting or luminescence radiation coming from the center of the sphere (the locus of the sample) back to the center. Thus the observed radiance flux, for example of Raman radiation, is greatly enhanced.

2. The mirrors of the surface of the sphere have their center of curvature at the locus of the sample. Therefore they need not to be adjusted specially. They also do not contaminate.

3. The adjustment of the sphere with respect to the spectrometer is done by 'reverse illumination': The radiation from a light source at the locus of the entrance slit is sent back to this locus, when the adjustment is perfect.

4. The adjustment of the illuminating beam is accomplished analogously: The paths to and from the sample are identical.

Examples of the invention are given in the accompanying drawings, they are described in the following paragraphs.

FIG. 1 shows a spherical sample cell.
FIG. 2 shows a sample arrangement for liquids.
FIG. 3 shows a flow cell with cylindrical sample.
FIG. 4 shows a flow cell with spherical sample.
FIG. 5 shows a sample arrngement with a sample sealed in a tube.
FIG. 6 shows another example of the invented sample arrangement.
FIG. 7 shows another example of the invented sample arrangement for sealed sample containers.
FIGS. 8 and 9 show sample arrangements for inhomogeneous samples.
FIG. 10 shows a sample arrangement, especially for investigations of samples, included in a matrix.
FIGS. 11–13 shows sample arrangements for investigations by 'evanescent' waves.
FIG. 14 shows a sample arrangement with especially good heat conductivity.

FIG. 1 shows the cross-section of the spherical sample arrangement. It contains in the center the sample 2. The radiation, emitted by the sample into the cone 3 is analysed by the spectrometer. Luminescence of the sample can be excited using angles of 0, 90, 180 degrees (4, 5, 6) or any other angle between the illuminating and the observed beam.

Variations of this basic concept are described by the following examples.

A sample arrangement for Raman spectrometry of liquids is shown in FIG. 2. A sphere 1 of transparent material, e.g. saphire, contains a liquid sample 2 in its center. A positive lens 7 focuses the illuminating (laser) radiation into the center of the sphere. This radiation then hits the mirror 8 on the surface of the sphere which reflects the beam back to the center. The Raman radiation, which is sent from the sample into the cone 3 is collected by the entrance optics of the spectrometer. The radiation which is sent from the sample into the opposite direction is reflected back to the sample by the mirror 9 on the surface of the sphere and is therefore additionally collected by the entrance optics of the spectrometer. Mirrors 8 and 9 accomplish an increase of the Raman radiation, analysed by the spectrometer by a factor of about 4. The figure of merit is increased additionally when the surface of the sphere is provided with an anti-reflection coating in the window areas 10 in order to reduce reflexion.

Variation of the arrangement according to FIG. 2 are shown in FIGS. 3–7, as cross-section A–B in FIGS. 3–6.

FIGS. 3 and 4 show flow cells with a cylindrical 2A (FIG. 3) or spherical 2B (FIG. 4) arrangement of the samples in spheres 1A and 1B, respectively. They are produced by drilling or combining of two prefabricated half spheres. They are useful for the detection of samples by means of their luminescence (chemiluminescence, fluorescence, phosphorescence, Tyndall-, Rayleigh-, Mie- or Raman-scattering), for process-control or automatic sampling. The sample may be present at different pressures and temperatures. The same cells may also be used for optimal matching of micro samples to powerful infrared or UV/VIS spectrometers which measure absorption spectra.

FIG. 5 shows the sample 2C in a capillary (melting-point) tube 12, which is brought into optical contact with the sphere by means of a drop of immersion fluid.

FIG. 6 shows a sample cell 2D, which may be closed with a stopper 13.

FIG. 7 shows a modification of FIG. 5. Both allow the non-destructive investigation of precious, sensitive, or aggressive samples 2E in sealed containers. FIG. 7 is especially well suited for the control of products in sealed ampoules 14, for instance in the pharmaceutical industry as well as for the inspection of raw or polished jewels. The exciting radiation can be sent along the paths 5 or 6. The sample to be investigated is immersed in a suitable fluid 12. The sample arrangement of FIG. 7 may be used separated from the spectrometer, but connected to it optically by fiber optics.

For the investigation of luminescence spectra of crystal powders or other, especially inhomogeneous, samples the variations according to FIGS. 8 and 9 may be used. The sample arrangement is made from two transparent half spheres 1G, 1F with a half-spherical hole in the center of each half sphere. The half spheres are separated by a sample holder 17 which serves to space apart the two half spheres and to maintain the sample between the half spheres of the container. Spacer 17 whereat it contacts the samples container 2′ is advantageously provided with a reflecting inner surface. The half sphere 15 is completely covered with a mirror except a small window for the illumination of the sample 2F by a laser beam. This is also true for the half sphere 16, but the window for the emerging luminescence radiation has to be larger. The mirrors reflect the exciting and luminescence radiation which is not analysed by the spectrometer, back to the sample. Thus the intensity of the radiation analysed by the spectrometer, is increased considerably. The arrangement according to FIG. 8 uses sample holders of different thickness. The arrangement according to FIG. 9 allows the adjustment of the optimal thickness of the sample by transversal moving of the sample holder in the direction of the arrow. The half spheres in FIG. 9 comprise half sphere 1F and 1G.

FIG. 10 shows a sample arrangement consisting of a sphere 1H in which a cone is cut, the angle of which is somewhat larger than that of the light cone 'seen' by the spectrometer. The whole spherical surface is covered with a mirror 19, except for a small window for the laser beam which is used to excite luminescence along a path such as 4 or 5 shown in FIG. 1. The sample 2G is evaporated into the vertex of the cone at the center of the sphere alone or as a mixture with a matrix-forming substance. By contact with a cooling equipment the temperature of the sample arrangement may be decreased down to the region of absolute zero (matrix isolation technique).

Gaseous samples are arranged in a hollow sphere which may be covered with a mirror or surrounded by spherical mirrors analogous to FIG. 2.

For the excitation of luminescence spectra by 'evanescent waves' a technique similar to the ATR-technique (attenuated total reflection) for infrared spectroscopy may be used, FIGS. 12–13. FIG. 11 shows a sample 2H in contact with a half sphere 1I, the refractive index of which has to be larger than that of the sample. The locus of the total reflection is at the focus of the exciting beam. The evanescent wave reaching into the optically thinner medium excites a luminescence spectrum which is observed analogously as with the other arrangements. Like the arrangements, shown in FIGS. 3 and 4 it can be used for the detection of samples separated by chromatography. According to FIG. 12 the sample 2J in contact with half sphere 1I can be a material 21 which extracts specific components from a sample stream. It may be advantageous to observe the radiation emerging from the sample 2J through a second half sphere 1J in the opposite direction see FIG. 13. In FIG. 12 reference numeral 20 represents a through flow cuvette and reference numeral 11 a probe conductor.

The microscopy of a sample surface by luminescence radiation one point of the sample surface is illuminated by the focus of a laser beam under 90, 180 degrees or some other angle with respects to the direction of observation. The luminescence radiation emerging from this point is analysed by the spectrometer. By definite moving the sample in two or three dimensions the spectra of many volume elements of the sample may be observed and stored by a computer connected with the spectrometer. They can be arranged to images of the sample in the light of different spectral lines. The resolution of this microscope is determined essentially by the dimensions of the focal region of the laser beam. The thermal stress of the sample can bre reduced by contacting it with a transparent half sphere 1K, made from a good heat-conducting material, e.g. saphire as in FIG. 14, by means of an immersion liquid 12. In FIG. 14 reference numeral 2K represents the object of the microspectrometer.

For all variants the luminescence may be exicted by linear or circular polarized light and the state of polarization of the luminescence radiation may be analysed. In this way information about the polarization properties of the sample, its orientation or its chiral properties may be collected.

Raman spectra of absorbing samples can be investigated, as is well known, without the danger of decomposition of the sample by a rotation of the sample, providing only a short exposure of the sample elements by the laser beam. This may also be accomplished by a rotation of the sample arrangement according to FIGS. 5-7 about appropriate axes.

I claim:

1. Sample arrangement for spectrometry, especially for Raman spectrometry, comprising an essentially spherical container of transparent solid material, and a sample at the center of the spherical container, said spherical container having an outer surface, light illuminated and light exiting portions of which define windows provided with anti-reflection coatings and having light reflecting layers on other surface portions of said outer surface of said spherical container, said container comprising two separate half spheres, the sample being provided in a separate sample holder serving to space apart said two half spheres and to maintain the sample between the half spheres of the container a the center thereof, the sample holder having an axis perpendicular to planar surfaces of the half spheres.

2. The device of claim 1, wherein the sample is gaseous, liquid or solid.

3. The device of claim 2, wherein the sample is polycrystalline, monocrystalline or amorphous.

4. Sample arrangement for spectrometry, especially for Raman spectrometry, comprising an essentially spherical container of transparent solid material, and a sample at the center of the spherical container, said spherical container having an outer surface, light illuminated and light exiting portions of which define windows provided with anti-reflection coatings and having light reflecting layers on other surface portions of said outer surface of said spherical container said container being formed with a cone-shaped hole which extends at least to the middle of the container with the angle of the cone approximately equal to the aperture angle of the imaging optics.

5. Sample arrangement for Raman spectrometry, comprising a half sphere container having a planar surface, a sample on said planar surface, and an anti-reflection coating on the spherical surface, said sample contacting the planar surface of the half sphere through the intermediary of an immersion fluid, and a holder for said sample adapted for two dimensional translation of the sample.

6. Sample arrangement for spectrometry, especially for Raman's spectrometry, comprising an essentially spherical container of transparent solid material, and a sample at the center of the spherical container, said spherical container having an outer surface, light illuminated and light exiting portions of which define windows provided with anti-reflection coatings and having light reflecting layers on other surface portions of said outer surface of said spherical container said sample being in a sealed holder matched to the arrangement by a half spherical hole in the center of the holder and an immersion fluid.

7. Sample arrangement for spectrometry, especially for Raman spectrometry, comprising an essentially spherical sample container of transparent solid material, and a sample at the center of the spherical container, wherein the sample is provided in a separate sample holder and the spherical container is made of two separate half spheres, said sample holder being arranged between the half spheres and having an axis perpendicular to planar surfaces of the half spheres.

8. Sample arrangement for Raman spectrometry, comprising a half sphere container having a planar surface, a sample on said planar surface, and an anti-reflection coating on the spherical surface, said sample being in a sealed holder matched to the arrangement by a half spherical hole in the center of the holder and an immersion fluid.

* * * * *